United States Patent [19]

Anderson-Mauser

[11] Patent Number: 5,360,718
[45] Date of Patent: Nov. 1, 1994

[54] DIAGNOSIS OF CANDIDA VAGINITIS BY DETECTING D-ARABINITOL IN VAGINAL FLUID

[75] Inventor: Linda Anderson-Mauser, Elkhart, Ind.

[73] Assignee: Miles Inc., Elkhart, Ind.

[21] Appl. No.: 151,318

[22] Filed: Nov. 10, 1993

Related U.S. Application Data

[63] Continuation of Ser. No. 839,176, Feb. 20, 1992, abandoned.

[51] Int. Cl.$^5$ .............................. C12Q 1/32; C12N 1/00
[52] U.S. Cl. ............................................ 435/26; 435/4; 435/295; 435/852; 435/921; 436/518; 436/904
[58] Field of Search ..................... 435/26, 4, 295, 810, 435/852, 921, 975; 436/518, 904

[56] References Cited

PUBLICATIONS

Soyama et al, *Clin. Chem. Acta*, vol. 149, pp. 149–154, 1985.
Wong et al, *J. Clin. Microbiol.*, vol. 26, No. 9, pp. 1670–1674, Sep. 1988.
Wong et al, *J. Infectious Diseases*, vol. 146, No. 3, pp. 353–359, Sep. 1982.

*Primary Examiner*—Michael G. Wityshyn
*Assistant Examiner*—Abdel A. Mohamed
*Attorney, Agent, or Firm*—Andrew L. Klanitter; Jerome L. Jeffers

[57] ABSTRACT

A method for the presumptive detection of Candida in vaginal fluid, thereby providing an aid to the diagnosis of Candida vaginosis. A sample of vaginal fluid is combined with a test composition comprising an indicator system that provides a chromogenic response in the presence of D-arabinitol; the detection of an elevated level of D-arabinitol indicating the presumptive presence of Candida. The test composition preferably comprises the enzyme D-arabinitol dehydrogenase, NAD, an electron transfer agent, and a chromogenic indicator.

7 Claims, 1 Drawing Sheet

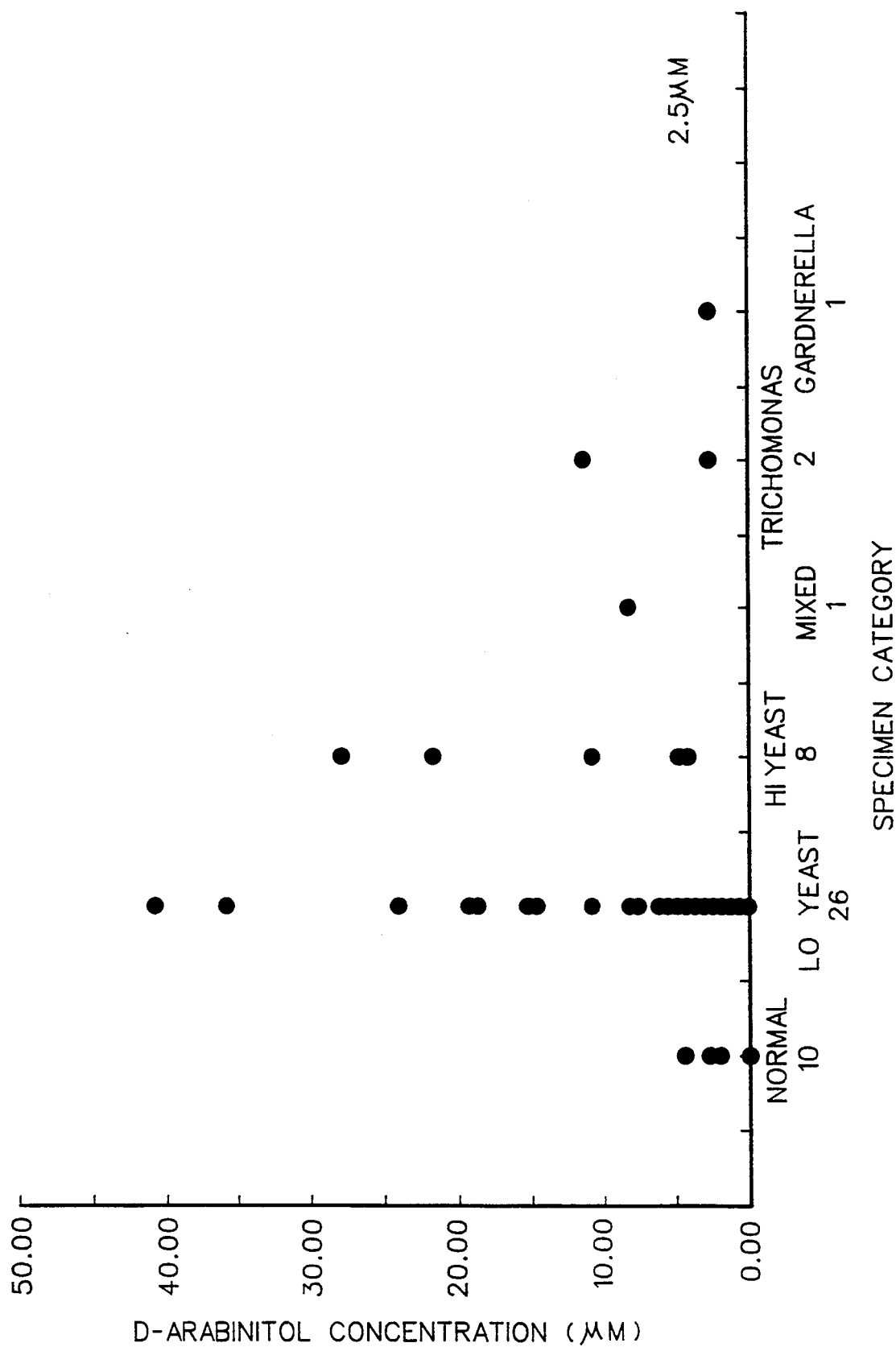

DIAGNOSIS OF CANDIDA VAGINITIS BY DETECTING D-ARABINITOL IN VAGINAL FLUID

This is a continuation of application Ser. No. 839,176, filed on Feb. 20, 1992, now abandoned.

BACKGROUND OF THE INVENTION

The present invention relates to the diagnosis of Candida vaginosis. In particular, the invention concerns the presumptive detection of Candida in vaginal fluid by means of a chemical assay.

*Candida albicans* and related species can inhabit mucocutaneous body surfaces and are considered endogenous anorectal flora. Vaginal infections caused by *Candida sp.* occur due to changes in vaginal ecology brought on by an increase in estrogen, as may occur during premenses, pregnancy, oral contraception, treatment with broad spectrum antibiotics or treatment with steroids. Also, women with immune dysfunction, diabetes or multiple sexual partners are at an increased risk of developing Candida-caused vaginitis. In these instances, this normal mucocutaneous commensal may overgrow the predominant Lactobacillus flora of the vagina and cause "candida vaginitis," also known as vaginal candidosis. This localized infection is the most commonly reported genital infection in women attending genito-urinary medicine and sexually transmitted disease clinics (Laboratory Methods for the Diagnosis of Sexually Transmitted Diseases; Eds. B. Wentworth and F. Judson, Am. Pub. Hlth. Assoc., Washington, D.C., 1987).

Although effective treatment of Candida-caused vaginitis relies on making an accurate diagnosis, treatment of a patient is often based simply on the patient's verbal description of the malady or symptoms. Whereas a physical examination may reveal the classic discharge described as the consistency of cottage cheese, patients many times do not present with classic symptoms. Additionally since vaginal infections may have other microbial etiology, there is need for alternative approaches to differential diagnosis, i.e., in addition to patient symptoms and physical examination. Since diagnosis is generally made during an office visit, simple methods are needed to enable rapid confirmation of clinical information. Methods currently in place in physicians' clinics to provide differential diagnosis of vaginal infections include measurement of vaginal pH, microscopic examination of Gram stains and potassium hydroxide (KOH) wet mounts, and KOH generation of an amine odor. The diagnosis of Candida-caused vaginitis generally is made on the basis of a 10% KOH smear with identification of pseudohyphae (yeast). In most cases, the quantity of yeast is higher in vaginal fluid from patients with a Candida vaginitis than in fluid from asymptomatic women colonized by Candida. Unfortunately, with a reported level of only 38% correlation of microscopy with correct diagnosis (R. Rajakumar, et al., Use of Slide Latex Agglutination Test for Rapid Diagnosis of Vaginal Candidosis, Genitourin. Med. 63:192–195, 1987), microscopy is a relatively poor aid to the diagnosis o Candida vaginitis.

The molecular characteristics of Candida antigens present in tissue and serum during systemic invasion of the body by Candida (a medical condition known as candidiasis or candidosis) are well reported in the literature. (C. Lemieus, G. St-Germain, et al., Collaborative Evaluation of Antigen Detection by a Commercial Latex Agglutination Test and Enzyme Immunoassay in the Diagnosis of Invasive Candidiasis, J. Clin. Microbiol. 23:249–253, 990; L. Zoller, I. Kramer et al., Enzyme Immunoassays for Invasive Candida Infections: Reactivity of Somatic Antigens of *Candida albicans*, J. Clin. Microbiol. 29:1860–1867, 1991; R. Matthews and J. Burnie, Diagnosis of Systemic Candidiasis by an Enzyme-Linked Dot Immunobinding Assay for a Circulating Immunodominant 47-Kilodalton Antigen, J. Clin. Microbiol. 26:459–463, 1988). However, a comparatively small amount of research has been conducted to identify Candida antigens present in vaginal fluid of patients with Candida vaginitis. Recently, however, several immunoassays have been developed for Candida vaginitis diagnosis. For example, Mercia Diagnostics Ltd., Surrey, UK, has commercialized an immunoassay which employs Candida-reactive antibody-coated latex beads; the beads agglutinate (appear as visible clumps) when a suspension of the latex beads are brought into contact with Candida antigens present in vaginal fluid. Although latex agglutination assays are relatively simple to perform, their poor cost/benefit ratio has minimized their use, i.e., diagnosticians consider test cost too high for the diagnostic benefit they pose. A number of the immunoassays are based upon detection of Candida cell wall mannan (W. J. Pike, J. Clarke et al., Candida Cell Wall Mannan in the Vagina and its Association with the Signs and Symptoms of Vaginal Candidosis. J. Med. and Vet. Mycol. 29:305–312, 1991).

Studies of systemic or invasive Candida infection have shown that D-arabinitol is a major metabolite appearing in urine and serum (J. M. Jones, Laboratory Diagnosis of Invasive Candidiasis, Clin. Microbiol. Rev. 3:32–45, 1990) It has also been shown that the serum and urine levels of this metabolite depend on the efficiency of its production by yeast during the systemic infection and on the mode and rate of elimination of the metabolite by the host (E. Bernard et al, Rate of Arabinitol Production by Pathogenic Yeast Species, J. Clin. Microbiol. 14:189–194, 1981). See also J. W. Gold et al, Serum Arabinitol Concentrations and Arabinitol/Creatinine Ratios in Invasive Candidiasis, J. Infect. Dis. 147:504–513, 1983. D-Arabinitol in the sera of patients with candidiasis has been measured by gas-liquid chromatography (T. E. Kiehn et al, Candidiasis: Detection by Gas-Liquid Chromatography of D-Arabinitol, a Fungal Metabolite, in Human Serum, Science 206:577–580, 1979) and by enzymatic assay with D-arabinitol dehydrogenase (K. Soyama and E. Ono, Enzymatic fluorometric method for the determination of D-arabinitol in serum by initial rate analysis, Clin. Chim. Acta 149:149–154, 1985; and B. Wong and K. L. Brauer, Enantioselective Measurement of Fungal D-Arabinitol in the Sera of Normal Adults and Patients with Candidiasis, J. Clin. Microbiol. 26:1670–1674, 1988).

Arabinitol has also been reported to appear in the urine of diabetic and uremic patients (E. Pitkanen, Clin. Chim. Acta 38:221–230, 1972), although it may be that such appearance of arabinitol was due to low grade Candida infections in the patients studied.

SUMMARY OF THE INVENTION

It has now been found that Candida-caused vaginitis can be presumptively identified by the simple chromogenic detection of D-arabinitol in vaginal fluid. The method involves the combination of a sample of vaginal fluid with a test composition comprising an indicator system that produces a chromogenic response to the presence of D-arabinitol. Such test composition preferably comprises the enzyme D-arabinitol dehydrogenase, the enzyme cofactor nicotinamide dinucleotide (NAD), an electron transfer agent, and a chromogenic indicator that produces a color change in the presence of reduced NAD (NADH) and the electron transfer agent. The presence of increased levels of D-arabinitol in vaginal fluid correlates with Candida vaginitis in patients. In contrast with urine and serum samples which are normally sterile, vaginal fluid samples will be expected to contain products and debris from a variety of flora; however, it has been found that significant metabolism of Candida-originating D-arabinitol does not occur.

The ability to rapidly and simply detect D-arabinitol in vaginal fluid specimens significantly aids in the diagnosis of Candida vaginitis. Such a test method provides a number of important advantages over the prior diagnostic methods. For example, the detection of the simple D-arabinitol metabolite does not require that intact and viable cells be isolated from the patient as is required by classical methods based on culture. In addition, typical microscopy methods require significant training of the reader and the ability to obtain a sample that contains an observable number of organisms, e.g., at least $10^5$ per milliliter. Moreover, it has been found that the multitude of extraneous substances present in vaginal fluid specimens produce no significant interference with the D-arabinitol dehydrogenase enzymatic reaction. Accordingly, a chromogenic assay is possible which can be very simply performed by relatively untrained individuals in a physician's office or clinic.

BRIEF DESCRIPTION OF THE DRAWINGS

The FIGURE is a graph showing the results of a clinical study correlating levels of vaginal fluid D-arabinitol with the clinical status of the patient.

DESCRIPTION OF THE PREFERRED EMBODIMENTS

The vaginal sample can be obtained from a patient by a variety of known methods and can be brought into contact with the test composition with or without processing. Typically, the sample will be obtained by swab which can then be used to directly contact the sample with the test composition, e.g., by immersing the swab in a liquid containing one or more of the test reagents or by rolling or otherwise contacting the swab with the surface of a test device, e.g., test strip, in or on which one or more of the test reagents are disposed. Another approach involves the immersion of the swab into a processing or extraction liquid, e.g., comprising buffers, preservatives, or the like, and removal of an aliquot of supernatant, either after filtration, centrifugation, or the like to remove particulate debris, or simply after allowing debris to settle by gravity. The aliquot of supernatant is then contacted with the test composition as above. In general, the method by which the sample is obtained and processed, if at all, is not critical and can be selected according to the particular needs or desires of the user.

In general, any test composition that will provide a chromogenic response in the presence of D-arabinitol can be used as the test composition in the present method. Normally, the test reaction will be enzymatic and involve an enzyme such as D-arabinitol dehydrogenase (ADH). Such enzyme is characterized by catalysis of the oxidation of D-arabinitol in the presence of NAD with the resulting reduction of NAD to NADH. Suitable enzymes are available from a variety of sources, and most commonly will be microbial in origin. Microbial-derived ADH can be obtained by isolation and purification of the enzyme protein from suitable bacteria, yeast, fungi, or the like, e.g., *Enterobacter aerogenes* or *Klebsiella pneumoniae*, or from a strain containing a recombinant expression vector into which the gene encoding ADH, or an active fragment thereof, has been inserted by means of genetic engineering.

When using an ADH assay, the produced NADH can be detected or measured, qualitatively or quantitatively, either directly by its native color (absorption at about 340 nm), or by further reaction of NADH to produce a chromogenic species. Commonly, NADH can be determined by reaction with a variety of chromogenic indicators in the presence of a conventional electron transfer agent. Indicators and electron transfer agents that are suitable for this purpose are well known in the art. Typically, the indicator is a tetrazolium salt such as 2-(4-iodophenyl)-3-(4-nitrophenyl)-5-phenyl-tetrazolium chloride (INT), 3-(4,5-di-methylthiazol-2-yl)-2,5-diphenyltetrazolium chloride (MTT), 2,2',5,5'-tetraphenyl-3,3'-(3,3'-dimethoxy-4,4'-diphenylene) ditetrazolium chloride (NBT), and derivatives and modifications thereof. Representative of electron transfer agents are diaphorase (dihydrolipoamide reductase EC 1.6.4.3), 5-methylphenazinium methyl sulfate (PMS) and derivatives and modifications thereof, and the like. The choices of indicator and electron transfer agent are not critical and can be left to the desires and needs of the ordinary skilled worker. Further background regarding such detection systems can be found in the literature, e.g., Babson et al, Clin. Chim. Acta 12:210–215 (1965), Gay et al Clin. Chem. 14:740–753 (1968), and Gapps II et al, Clin. Chem. 12:406–413 (1966).

A particularly useful form of test composition is that of a test strip, i.e., a test device comprising a carrier substrate incorporated with the test composition. Suitable carrier substrates, as well as methods and structures for incorporating the test composition components with such carrier substrates are within the ordinary skill in the art. Examples of carrier substrates are absorbent or bibulous matrices such as filter paper, fleeces, porous and absorbent paper, cloth, glass fiber filters, polymeric membranes and films, and the like. Incorporation methods include impregnation of a formed carrier matrix with a solution, suspension, or other liquid form of the test composition, in one or more steps, followed by drying of the matrix; formation of a matrix in the presence of one or more of the components of the test composition, e.g., by casting or layering solutions of film or membrane forming formulations.

The present invention will now be illustrated, but is not intended to be limited by, the following examples.

EXAMPLES

Assay Reagents

A commercially available test for serum D-arabinitol was used (LABOFIT, Nakaraidesuku Co., Ltd, Kyoto, Japan). This method is based on the oxidation of D-arabinitol by D-arabinitol dehydrogenase to D-xylulose with concomitant reduction of NAD to NADH. The produced NADH is then reoxidized to NAD through the coupled reaction of resazurin (a fluorogenic hydrogen ion acceptor) and the electron transfer agent diaphorase. The reduction product resorufin can be measured fluorimetrically with excitation at 560 nm and emission at 580 run.

Assay Method

Vaginal fluid specimens were obtained from 69 persons attending a clinic for routine gynecological examination or for diagnosis of suspected gynecologic infection. Specimens are processed as follows: vaginal exudate was obtained on a cotton or dacron swab, the swab was immersed in 0.5 milliliter (mL)–1.0 mL of saline (0.9% NaCl in water) and agitated to detach the exudate and to suspend/solubilize the material in the saline. Following microscopic observation of an aliquot of the fluid (fluid was placed on a microscope slide and viewed under a microscope), the fluid was frozen at −20° C.

In the usual procedure for assay reaction, the frozen fluid was thawed and, if cloudy, centrifuged 5 minutes at 12,000× g. One-hundred microliters (100 μL) of this saline-extracted specimen was mixed in a 4 mL cuvette with 2.0 mL Tris-HCl buffer (0.6 molar (M), pH 9.0) and 200 μL of distilled water. To this mixture was added 500 μL of the luminescent solution (diaphorase, NAD, and sodium resazurin). This mixture was heated to 37° C. and transferred to a fluorometer cuvette chamber for a background fluorescence check. Subsequently 50 μL D-arabinitol dehydrogenase was added to the cuvette. Excitation readings were taken at 15 seconds, 30 seconds, 2 minutes, and 3 minutes after enzyme addition to enable determination of a fluorescence rate measurement.

Results

The results of these studies are shown in the drawing. The gynecological diagnostic categories of the 69 patients involved in the study, with the exception of "Normal", are defined by the original microscopic diagnosis. For all categories except "Normal," patients exhibited some symptom of vaginal infection which caused them to seek a gynecologic diagnosis. Patients included in the "Normal" category attended the clinic for routine gynecologic examination and exhibited no symptoms of vaginal infection. The results demonstrate that D-arabinitol can be measured in 100% (8/8) of specimens having a microscope diagnosis of large amounts of Candida. When the microscopic diagnosis indicated a low bioload of Candida, the Candida metabolite was detected and measured less frequently (26/45 or 58%). Given the poor correlation of microscopy with actual disease, these results are not significant. Detection of D-arabinitol in a specimen said to contain Trichomonas may only indicate that the microscopist discontinued slide reading when this motile organism was observed. Importantly, D-arabinitol was not detected in "Normal" specimens. The dotted line indicates the lower limit of test sensitivity (2.5 μM).

The present invention has been particularly described and exemplified above. Clearly, many other variations and modifications of the invention can be made without departing from the spirit and scope hereof.

What is claimed is:

1. A method for the diagnosis of Candida vaginitis, comprising the steps of:
   (a) combining a sample of vaginal fluid with a test composition comprising an indicator system that produces a chromogenic response in the presence of D-arabinitol, and
   (b) observing said chromogenic response for elevated levels of D-arabinitol in said sample.

2. The method of claim 1 wherein said sample is obtained by a swab.

3. The method of claim 2 wherein said swab is immersed in an extraction liquid and an aliquot of the supernatant is combined with said test composition.

4. The method of claim 1 wherein said test composition comprises D-arabinitol dehydrogenase.

5. The method of claim 4 wherein said test composition further comprises nicotinamide dinucleotide (NAD), an electron transfer agent, and a chromogenic indicator that produces a color change in the presence of reduced NAD and said electron transfer agent.

6. The method of claim 4 wherein said D-arabinitol dehydrogenase is a bacterial enzyme.

7. The method of claim 6 wherein said bacterial enzyme is derived from *Enterobacter aerogenes*.

* * * * *